United States Patent [19]

Luft et al.

[11] Patent Number: 4,952,727

[45] Date of Patent: Aug. 28, 1990

[54] PROCESS FOR THE PREPARATION OF MONOCARBOXYLIC ANHYDRIDES

[75] Inventors: Gerhard Luft, Mühltal; Peter Trabold, Dieburg, both of Fed. Rep. of Germany

[73] Assignee: Hoechst Aktiengesellschaft, Hurt Knapsack, Fed. Rep. of Germany

[21] Appl. No.: 318,679

[22] Filed: May 3, 1989

[30] Foreign Application Priority Data

Mar. 17, 1988 [DE] Fed. Rep. of Germany ....... 3808867

[51] Int. Cl.$^5$ .............................................. C07C 51/54
[52] U.S. Cl. .................................................. 562/891
[58] Field of Search ........................................ 562/891

[56] References Cited

U.S. PATENT DOCUMENTS 4,657,884  4/1987  Luft et al. ........................... 502/161
4,776,987  10/1988  Luft et al. .

FOREIGN PATENT DOCUMENTS 0180799  11/1987  European Pat. Off. .

*Primary Examiner*—Paul J. Killos
*Attorney, Agent, or Firm*—Connolly and Hutz

[57] ABSTRACT

In the process for the preparation of monocarboxylic anhydrides of the general formula (RCO)$_2$O by reacting a carboxylic acid ester of dialkyl ether of the general formula RCOOR or ROR, where R in each case denotes the same alkyl radical having 1 to 4 carbon atoms, with carbon monoxide in the gas phase in the presence of iodine or bromine or compounds thereof as reaction promoter, and in the presence of a supported catalyst, at temperatures of from 130° to 400° C. and pressures of from 1 to 150 bar, where, in the supported catalyst, an organosilicon compound is bonded, as a polyfunctional coupling agent, on the one hand to a support material and on the other hand to a noble-metal compound from group VIII of the Periodic Table, a chelate-forming organosilicon compound of the general formula

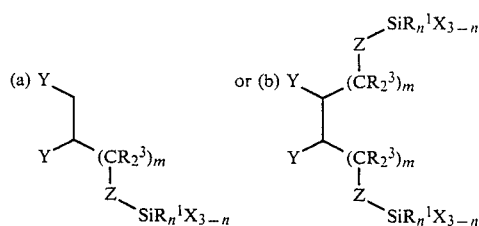

is employed as the polyfunctional coupling agent, where X=Cl, Br or —OR$^2$;
Y=—NR$_2^4$, a nitrogen-containing aryl radical, —PR$_2^4$, AsR$_2^4$, —SR$^4$ or —SH;
Z=zero, arylene or phenylene (optionally ortho-, meta- or para-substituted),
R$^1$=C$_1$ to C$_5$-alkyl;
R$^2$=C$_1$ to C$_5$-alkyl or —C$_6$H$_5$;
R$^3$=—H or C$_1$ to C$_3$-alkyl;
R$^4$=C$_1$ to C$_5$-alkyl, C$_5$ or C$_6$-cycloalkyl or —C$_6$H$_5$ or —CH$_2$C$_6$H$_5$, which are optionally substutited by halogen, methoxy, ethoxy or C$_1$ to C$_3$-alkyl groups;
n=0 or 1 or 2;
m=2 to 6, preferably 2 to 4.

17 Claims, No Drawings

PROCESS FOR THE PREPARATION OF MONOCARBOXYLIC ANHYDRIDES

The invention relates to a process for the preparation of monocarboxylic anhydrides of the general formula (RCO)₂O by reacting a carboxylic acid ester or dialkyl ether of the general formula RCOOR or ROR, where R in each case denotes the same alkyl radical having 1–4 carbon atoms, with carbon monoxide in the gas phase in the presence of iodine or bromine or compounds thereof as reaction promoter, and in the presence of a supported catalyst, at temperatures of from 130° to 400° C. and pressures of 1–150 bar, where, in the supported catalyst, an organosilicon compound containing alkoxy or halogen groups and containing organonitrogen, organophosphorus, organoarsenic, organosulfur or mercapto groups, is bonded, as a polyfunctional coupling agent, on the one hand to a support material and on the other hand to a noble-metal compound from group VIII of the Periodic Table.

A process of this type which operates in the gas phase using a supported catalyst has already been disclosed in German Offenlegungsschrift No. 3,440,647 A1, which avoids the disadvantages occurring in liquid-phase processes, for example the difficult separation and recycling of suspended and, in some cases, dissolved catalyst and, where appropriate, promoter.

In addition, German Offenlegungsschrift No. 3,511,050 A1 discloses a very similar process, but one in which the support material in the supported catalyst has simply been impregnated with the solution of a noble metal chelate compound formed from the noble-metal compound and a chelating agent containing organonitrogen, organophosphorus, organoarsenic, organosulfur or mercapto groups.

The object of the present invention is to modify the chelating agent in a manner such that it acts as a polyfunctional coupling agent and that the service life (duration of activity) and selectivity of the supported catalyst clearly improve with the same support material.

In detail, the process of the invention comprises employing, as the polyfunctional coupling agent, a chelate-forming organosilicon compound of the general formula

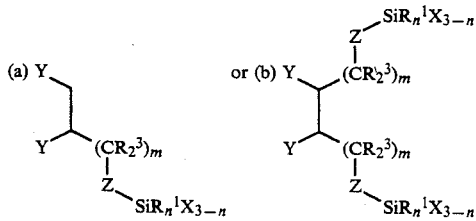

where
X = Cl, Br or —OR²;
Y = —NR₂⁴, a nitrogen-containing aryl radical, —PR₂⁴, AsR₂⁴, —SR⁴ or —SH;
Z = zero, arylene or phenylene (optionally ortho-, meta- or para-substituted),
R¹ = $C_1$ to $C_5$-alkyl;
R² = $C_1$ to $C_5$-alkyl or —C₆H₅;
R³ = —H or $C_1$ to $C_3$-alkyl;
R⁴ = $C_1$ to $C_6$-alkyl, $C_5$ or $C_6$-cycloalkyl or —C₆H₅ or —CH₂C₆H₅, which are optionally substituted by halogen, methoxy, ethoxy or $C_1$ to $C_3$-alkyl groups;
n = 0 or 1 or 2;
m = 2 to 6, preferably 2 to 4.

In addition, the process of the invention may optionally and preferably have the features that (a) the chelate-forming organosilicon compound in the supported catalyst is bonded, as the polyfunctional coupling agent, on the one hand to the support material and on the other hand alternately to the noble-metal compound and to a non-noble-metal compound from sub-group 6 or 8 of the Periodic Table of the Elements;

(b) the supported catalyst additionally contains, as promoters, non-noble-metal compounds from main groups 1 to 3 or sub-groups 4 to 6 or 8 of the Periodic Table of the Elements;

(c) the supported catalyst contains an inorganic oxidic support material or an activated charcoal support, whose residual active hydroxyl groups have been deactivated by esterification or etherification;

(d) the supported catalyst contains in total 0.01 to 50% by weight, preferably 0.1 to 20% by weight, of noble-metal compound, coupling agent and, where appropriate, non-noble-metal compound;

(e) the supported catalyst is employed in a grain size of from 1 to 20 mm.

Suitable catalyst supports are preferably inorganic oxides, such as, for example, $SiO_2$, $Al_2O_3$, $MgO$, $TiO_2$, $La_2O_3$, $ZrO_2$, zeolite, clay, $NiO$, $Cr_2O_3$, $WO_3$ or corresponding mixed oxides, but also activated charcoal, which have BET surface areas of 1–1000 m²/g, preferably 30–400 m²/g, and must always also contain active OH groups. These OH groups react with the functional group(s) X of the coupling agent to form oxygen bridges between the support and the coupling agent.

Again as in German Offenlegungsschriften Nos. 3,511,050 and 3,440,647, the promoters of main group 5 or 6 are chemically bonded in the coupling agents employed according to the invention. They themselves form a functional group which is chelated by the noble-metal compounds of group VIII and, where appropriate, non-noble-metal compounds of sub-group 6 or 8.

It is an advantage that the promoters of main group 5 or 6 of the Periodic Table of the Elements which are necessary to increase the catalyst activity and selectivity form a functional group Y in the polyfunctional coupling agents and can thus be immobilized to the maximum concentration, which is determined by the number of OH groups on the support surface. Separation and recycling of these, for example, organonitrogen or organophosphorus promoters is therefore superfluous.

The process of the invention for the preparation of monocarboxylic anhydrides has higher selectivities and longer service lives of the supported catalyst, particularly in the case of long-term use, than the known processes described in the introduction.

A further advantage of the process of the invention is that it offers the possibility of chemically immobilizing noble-metal chelates on the support surfaces. In addition, the modified noble-metal chelate compounds and, where appropriate, non-noble-metal chelate compounds applied to the support material exhibit even higher melting points (240°–270° C.) than the complexes described in German Offenlengungsschriften Nos. 3,440,647 and 3,511,050, which results in higher thermal stability of the catalysts and in an increase in the range of use of from 20° to 50° C.

The process of the invention is used, in particular, for the preparation of acetic anhydride from methyl acetate or dimethyl ether in the presence of methyl iodide or methyl bromide as reaction promoter. It is also possible to employ HI, HBr or generally RI or RBr as reaction promoter, where R represents an alkyl radical having 1–4 carbon atoms.

In the general formulae for the organosilicon compounds suitable as coupling agents (spacers), X preferably denotes —$OR^2$ and in particular methoxy or ethoxy. If n is not zero, $R^1$ denotes an unbranched alkyl radical, in particular methyl, ethyl or propyl.

The support materials have already been mentioned; suitable mixed oxides are, for example $Cr_2O_3$—$Al_2O_3$, $WO_3$—$Al_2O_3$, $MgO$—$Al_2O_3$, $SiO_2$—$Al_2O_3$ or $ZrO_2$—$Al_2O_3$. The supported catalyst preferably contains 0.05 to 5% by weight of noble metal.

Noble-metal compounds which can be employed in the preparation of the supported catalyst are, for example the following compounds:

Rhodium:
$RhCl_3$, $RhCl_3 \cdot 3 H_2O$, $RhBr_3$, $RhI_3$, $Rh(NO_3)_3$, $Rh_2(CO)_4Cl_2$, $Rh_2(CO)_4Br_2$, $Rh(CO)_4I_2$, $[P(C_6H_5)_3]_3RhCl$, $[P(C_6H_5)_3]_2Rh(CO)Cl$, $Rh_6(CO)_{16}$, $Rh_4(CO)_{12}$, $Rh_2(O_2CCH_3)_4$, $[RhCl(C_3H_{12})]_2$;

Iridium:
$IrCl_3$, $[Ir(CO)_3Cl]_2$, $Ir[P(C_6H_5)hd 3_2(CO)Cl$, $Ir_4(CO)_{12}$, $[IrCl(C_8H_{12})]hd 2$, $Cl(CO)_2Irpyr$ (pyr=$C_6H_5N$);

Palladium
$PdCl_2$, $PdBr_2$, $PdI_2$, $(CH_3CO_2)_2Pd[P(C_6H_5)_3]_2$, $PdCl_2[P(C_6H_5)_3]_2$, $Pd(O_2CCH_3)_2$, $PdCl_2(C_8H_{12})$, $(C_6H_5CN)_2PdCl_2$;

Ruthenium:
$RuCl_3$, $Ru_3(CO)_{12}$, $RuCl_2[P(C_6H_5)_3]_3$, $RuCl_2(CO)_2[P(C_6H_5)_3]_2$, $[RuCl_2(CO)_3]_2$.

Suitable non-noble-metal compounds from sub-group 6 or 8, in particular Cr, Ni, but also W, Fe or Co, which likewise react with the chelating agents are furthermore the following, for example:

Chromium:
$Cr(CO)_6$, $CrCl_3$, $C_7H_8Cr(CO)_3$.

Nickel:
$Ni(CO)_4$, $[P(C_6H_5)_3]_2Ni(CO)_2$, $NiCl_2$, $Ni(C_8H_{12})_2$.

Non-noble-metal compounds which can be employed from main groups 1 to 3 or sub-groups 4 to 6 or 8 of the Periodic Table, preferably of Li, Na, Mg, Ca, Al, Ti, Zr, V, Cr, W, Fe, Co, or Ni, are, for example, hydroxides, carbonates, carbonyls, hydrides, halides and other salts. These compounds of non-noble metals may be additionally applied to the catalyst support by impregnation, for example as a solution.

In order to prepare the supported catalyst employed according to the invention, it is first necessary to prepare the polyfunctional coupling agent, i.e. the chelate-forming organosilicon compound, containing the functional groups Y. This can be prepared analogously to literature references. In general, one of the noble-metal compounds mentioned from group VIII and, where appropriate, one of the non-noble-metal compounds mentioned from sub-group 6 or 8 is then connected, in solution, with the coupling agent, chelate compounds being produced which are suitable, due to their organosilicon function, for chemical immobilization.

This is followed by reactive adduction of the noble-metal-containing chelate with the OH groups of the support material with elimination of a group X as XH (for example HCl, HBr or $HOR^2$). This is accomplished by heating the components suspended in a non-polar solvent at the reflux temperature for 24 to 100 hours.

All further details on the syntheses can be found in the description of the catalyst preparation.

The mixing ratio of carboxylic acid ester or dialkyl ether and iodine (compound) or bromine (compound) in the reaction zone may vary within broad limits. In general, the amount of carboxylic acid ester and/or dialkyl ether is 1 to 500 moles, preferably 1 to 100 moles, per mole of iodine (compound) or bromine (compound). The temperature of the reaction zone is selected so that the reaction mixture is gaseous at any desired conversion. The temperature is preferably selected between 150° and 250° C. The preferred pressure is between 5 and 30 bar.

The residence time of the reaction mixture on the solid supported catalyst is 1 to 1000 seconds, preferably 1 to 180 seconds. The reaction can take place in a flow tube, which is preferably arranged vertically and packed with supported catalyst, or alternatively in a stirred or shaken autoclave containing the supported catalyst. The carbonylation is generally carried out under virtually anhydrous conditions; however, the presence of small amounts of water, as occur in the commercially available starting materials, is permissible, but should not exceed 1 mole %, based on the starting materials. Neither is the carbonylation impaired by small amounts of methanol in the starting materials. Hydrogen, which may be present in small amounts in commercially available carbon monoxide, also has little effect.

The reaction mixture flowing out of the carbonylation zone is gaseous and contains carbon monoxide, methyl iodide, acetic anhydride, unreacted methyl acetate or dimethyl ether and possibly small amounts of acetic acid. The gaseous reaction mixture is cooled, acetic anhydride and possibly acetic acid condense out, and the noncondensed substances, such as CO, methyl iodide, methyl acetate or dimethyl ether, are fed back into the reaction zone. The amounts of ester or ether and CO which have reacted are continuously replaced.

Simple separation of the anhydrides by cooling the reaction mixture flowing out and recycling the noncondensible gases, as in the known processes mentioned, represents an essential advantage since this can take place without complicated separation operations. The supported catalyst is not contaminated and remains in the reaction zone, which considerably simplifies the overall course of the process.

EXAMPLES

STIRRED AUTOCLAVE EXPERIMENTS

A 0.25 liter capacity stirred autoclave made from corrosion-free stainless steel (Hastelloy C), provided with the necessary inlet and outlet lines and containing a rotatable catalyst basket, is used.

The carboxylic acid esters or dialkyl ethers are reacted in the gas phase with CO gas in the presence of the agitated, solid supported catalyst. The supported catalyst is located in the rotatable catalyst basket, which simultaneously ensures thorough mixing of the gases.

The autoclave is charged with 2.5 ml of a liquid mixture comprising 20 parts by volume of methyl iodide and 80 parts by volume of ester or ether and is heated to the reaction temperature. The carbonylation is initiated by injecting carbon monoxide. The CO pressure is kept constant by regular re-injection.

The details on the experimental procedures can be seen from the examples.

EXAMPLE 1

2 ml (1.86 g) of methyl acetate, 0.5 ml (1.14 g) of methyl iodide and 7.2 g of catalyst No. 1 are reacted in the autoclave with carbon monoxide at a CO pressure of 15 bar and at 180° C. After a reaction time of 1 hour, a catalyst performance of 19.7 g $Ac_2O$/g of Rh per hour is obtained, at a selectivity of 95%.

EXAMPLE 2

2 ml (1.86 g) of methyl acetate, 0.5 ml (1.14 g) methyl iodide and 7.9 g of catalyst No. 2 are reacted in the autoclave with carbon monoxide at a CO pressure of 15 bar and 180° C. After a reaction time of 1 hour, a catalyst performance of 18.8 g of $Ac_2O$/g of Rh per hour is obtained, at a selectivity of 96%.

EXAMPLE 3

2 ml (1.86 g) of methyl acetate, 0.5 ml (1.14 g) of methyl iodide and 6.5 g of catalyst No. 3 are reacted in the autoclave with carbon monoxide at a CO pressure of 15 bar and at 180° C. After a reaction time of 1 hour, a catalyst performance of 41.0 g of $Ac_2O$/g of Rh per hour is obtained, at a selectivity of 89%.

FLOW-TUBE EXPERIMENT

EXAMPLE 4

A steel tube 20 mm in diameter and 400 mm in length is arranged vertically as a flow tube and packed with 50.6 g of catalyst number No. 1. At a pressure of 12 bar and a temperature of 180° C., 8 l (s.t.p.) per hour CO (1 (s.t.p.)=liters, measured at 1.013 bar and 0° C.) and an evaporated mixture (12.8 ml of liquid) of methyl iodide and methyl acetate (molar ratio 1:4) are passed through the flow tube.

The reaction mixture flowing out is analyzed on-line by gas chromatography. A space-time yield of 12.5 g of $Ac_2O$/g of Rh per hour is obtained here at a selectivity of 97%.

The carbonylation was carried out for 280 hours under these reaction conditions, the supported catalyst employed exhibiting no loss in activity.

DESCRIPTION OF THE CATALYST PREPARATION

In all cases, the catalyst support was previously dried for 10 hours at 200° C. and 0.1 mbar for activation. After application of the metal component, the catalysts were heated at the boiling point for 8 hours with chlorotrimethylsilane and subsequently dried at 0.1 mbar and 100° C. All the syntheses were carried out in an argon atmosphere with exclusion of atmospheric oxygen and water. All the solvents used were previously dried over 4 A molecular sieve or, if possible, dried using sodium benzophenone.

The symbol "φ" used in the formulae below represents the phenyl radical ($C_6H_5$).

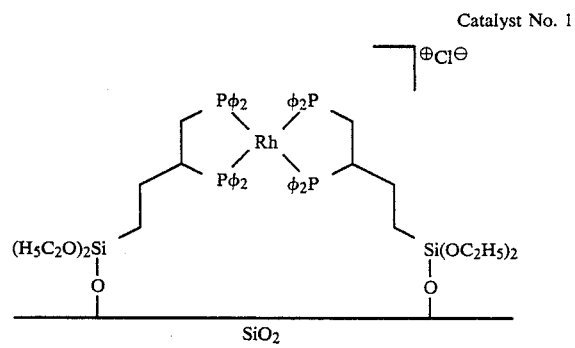

Catalyst No. 1

150 ml of a solution of 722 mg of complex 4 in toluene were added to 62.9 g of activated silicon dioxide pellets measuring ⅛"×⅛" (95% $SiO_2$) and having a BET internal surface area of 68 m²/g and a pore volume of 0.43 ml/g. The yellow suspension was refluxed for 24 hours, the solvent becoming completely colorless. After the toluene had been removed under reduced pressure, the catalyst was dried at 0.1 mbar and 150° C. for 6 hours and subsequently extracted for 24 hours in a Soxhlet apparatus with benzene. After extraction, no rhodium was detected in the benzene.

Characterization: pale yellow pellets
Rh content: 0.09% by weight
Synthetic route for rhodium complex 4
1,2-Dichloro-4-(triethoxysilyl)butane (2):

0.5 mol of tetraethoxysilane are added dropwise to 0.1 mol of 1-butenylmagnesium bromide (1) in 100 ml of tetrahydrofuran, and the mixture was refluxed for 5 hours. The suspension obtained is subsequently filtered, and the solvent is stripped off. The residue is taken up in dichloromethane, and chlorine is passed in at 0° C. until the solution becomes a pale yellow color. After the solvent has been stripped off and after subsequent vacuum distillation, 2 is obtained in a yield of 64%.

1,2-Bis(diphenylphosphino)-4-(triethoxysilyl)butane (3):

3 is synthesized by reacting twice the molar amount of sodium diphenylphosphide in dioxane with 2, dissolved in tetrahydrofuran, at room temperature [analogous to 1,2-bis(diphenylphosphino)ethane; see K. Issleib and D.-W. Müller, Chem. Ber. 92, 3175 (1959)]. Yield 72%.

[1,2-Bis(diphenylphosphino)-4-(triethoxysilyl)-butane]rhodium(I) chloride (4): 4 mmol of 3, dissolved in benzene, are added dropwise with stirring to a solution of 1 mmol of dichlorotetracarbonyldirhodium in benzene. Stripping off the solvent and recrystallization from hexane gas gives analytically pure complex 4. Yield 94%. Cf. the synthesis of [1,2-bis(diphenylphosphino)ethane]rhodium(I) chloride; A. Sacco et al., J. Chem. Soc. (London), 3274 (1964).

Catalyst No. 2

-continued

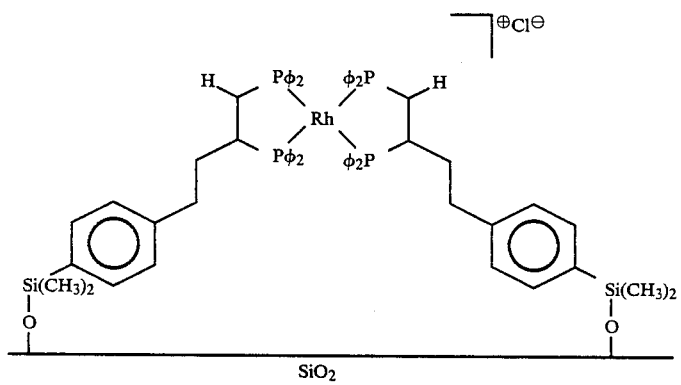

50 ml of 133 mg of complex 9 in toluene were added to 12.7 g of activated silicon dioxide pellets measuring ⅛"×⅛" (95% SiO₂) and having a BET internal surface area of 68 m²/g and a pore volume of 0.43 ml/g. The yellow suspension was refluxed for 24 hours, the solvent becoming completely colorless. After the toluene had been stripped off under reduced pressure, the catalyst was dried at 0.1 mbar and 150° C. for 6 hours and subsequently extracted for 24 hours in Soxhlet apparatus with benzene. After the extraction, no rhodium was detected in the benzene.

Characterization: pale yellow pellets
Rh content: 0.08% by weight
Synthetic route for rhodium complex 9
1,2-Dichloro-4-(4-chlorophenyl)butane (6):
  6 can be synthesized by reacting 4-(4-chlorophenyl)butene (5) with chlorine at 0° C. in dichloromethane. Yield 93%.

1,2-Bis(diphenylphosphino)-4-(4-chlorophenyl)butane (7):
  7 is synthesized by reacting twice the molar amount of sodium diphenylphosphide in dioxane with 6, dissolved in tetrahydrofuran, at room temperature in a yield of 82% [analogous to 1,2-bis(diphenylphosphino)ethane; see K. Issleib and D.-W. Müller, Chem. Ber. 92, 3175 (1959)].

1,2-Bis(diphenylphosphino)-4-[4-dimethylethoxysilyl)phenyl]butane (8):
  0.05 mol of 7 are converted in tetrahydrofuran into the arylmagnesium chloride compound [see R. D. Rieke and S. E. Bales, J. Am. Chem. Soc. 96, 1775 (1974); J. P. Collmann et al., J. Am. Chem. Soc. 105, 7288 (1983). 0.25 mol of diethoxydimethylsilane is subsequently added dropwise with stirring and ice cooling, and the mixture is allowed to warm to room temperature and finally refluxed for 5 hours. The reaction mixture is filtered; the solvent and excess diethoxydimethylsilane are stripped off in vacuo. The oily residue is crystallized from hexane, and 8 is obtained in a yield of 68%.

[1,2-Bis(diphenylphosphino)-4-[4-dimethylethoxysilyl)phenyl]butane]rhodium(I) chloride (9):
  4 mmol of 8, dissolved in benzene, are added dropwise with stirring to a solution of 1 mmol of dichlorotetracarbonyldirhodium in benzene. Stripping off the solvent and recrystallization from hexane gives analytically pure complex 9. Yield 95%. Cf. the synthesis of [1,2-bis(diphenylphosphino)ethane]rhodium(I) chloride; A. Sacco et al., J. Chem. Soc. (London), 3274 (1964).

Catalyst No. 3

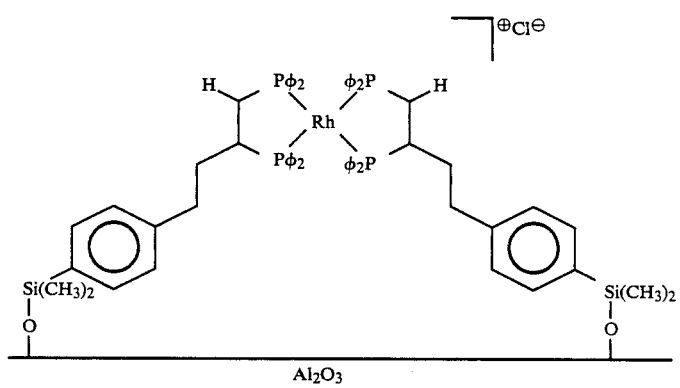

50 ml of 156 mg of complex 9 in toluene were added to 11.7 g of activated aluminum oxide beads (99% Al₂O₃) having a diameter of 3 mm, a BET internal surface area of 125 m²/g and a pore volume of 0.9 ml/g. The yellow suspension was refluxed for 24 hours, the solution becoming completely colorless. After the toluene had been stripped off under reduced pressure, the catalyst was dried at 0.1 mbar and 150° C. for 6 hours, and subsequently extracted for 24 hours in a soxhlet apparatus with benzene. After the extraction, no rhodium was detected in the benzene.

Characterization: pale yellow beads
Rh content: 0.1% by weight

We claim:
1. A process for the preparation of a monocarboxylic anhydride of the formula (RCO)₂O by reacting a car- boxylic acid ester or dialkyl ether of the formula RCOOR or ROR, where R in each case denotes the same alkyl radical having 1 to 4 carbon atoms, with carbon monoxide in the gas phase in the presence of iodine or bromine or an iodine or bromine compound, and in the presence of a supported catalyst, at a temperature of from 130° to 400° C. and a pressure of from 1 to 150 bar, where, in the supported catalyst, a chelate-forming organosilicon compound is bonded both to a support material and to a noble-metal compound from group VIII of the Periodic Table, said organosilicon compound being of the formula

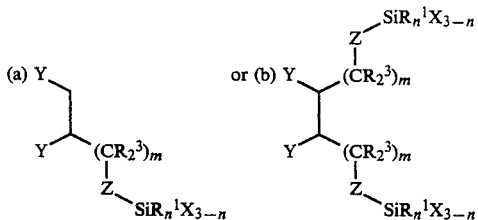

where
X=—Cl, —Br or —$OR^2$;
Y=—$NR_2^4$, a nitrogen-containing aryl radical, —$PR_2^4$, $AsR_2^4$, —$SR^4$ or —SH;
Z=arylene or phenylene, or Z is a direct bond, in which case the Si is bonded directly to $CR_2^3$;
$R^1$=$C_1$ to $C_5$-alkyl;
$R^2$=$C_1$ to $C_5$-alkyl or —$C_6H_5$;
$R^3$=—H or $C_1$ to $C_3$-alkyl;
$R^4$=$C_1$ to $C_6$-alkyl, $C_5$ or $C_6$-cycloalkyl or —$C_6H_5$ or —$CH_2C_6H_5$;
n=0 or 1 or 2;
m=2 to 6.

2. The process as claimed in claim 1, wherein, in the supported catalyst, chelate-forming groups of the chelate-forming organosilicon compound are also bonded to a non-noble-metal compound from the sub-group 6 or 8 of the Periodic Table of the elements.

3. The process as claimed in claim 1, wherein the supported catalyst additionally contains a non-noble-metal compound from main groups 1 to 3 or sub-groups 4 to 6 or 8 of the Periodic Table of the elements.

4. The process as claimed in claim 1, wherein the support material comprises an inorganic oxide or an activated charcoal, both containing active hydroxyl groups.

5. The process as claimed in claim 1, wherein the supported catalyst is supported by a material selected from the group consisting of $SiO_2$, $Al_2O_3$, MgO, $TiO_2$, $La_2O_3$, $ZrO_2$, zeolite, clay, NiO, $Cr_2O_3$, $WO_3$ or mixtures thereof.

6. The process as claimed in claim 1, wherein m has a value of 2, 3, or 4.

7. The process as claimed in claim 1 wherein the supported catalyst contains a total of 0.1 to 20% by weight, of noble-metal compound, coupling agent and, optionally non-noble-metal compound.

8. The process as claimed in claim 4, wherein said support material has a BET surface area of 1 to 1,000 $m^2/g$.

9. The process as claimed in claim 4, wherein said support material has a BET surface area of 30 to 400 $m^2/g$.

10. The process as claimed in claim 1, wherein said mono-carboxylic anhydride is acetic anhydride, said carboxylic acid ester or dialkylether is methyl acetate or dimethyl ether, respectively, and said iodine or bromine compound is methyl iodide, methyl bromide, HI, HBr, RI or RBr, wherein R is an alkyl radical having 1 to 4 carbons.

11. The process as claimed in claim 1, wherein X is —$OR^2$, methoxy, or ethoxy.

12. The process as claimed in claim 1, wherein if n is 1 or 2, $R^1$ is methyl, ethyl or propyl.

13. The process as claimed in claim 5, wherein said mixture is $Cr_2O$—$Al_2O_3$, $WO_3$—$Al_2O_3$, MgO—$Al_2O_3$, $SiO_2$—$Al_2O_3$, or $ZrO_2$—$Al_2O_3$ and where said supported catalyst contains 0.05 to 5% by weight of noble-metal.

14. The process as claimed in claim 1, wherein the supported catalyst contains a total of 0.01 to 50% by weight of noble-metal compound, coupling agent and, optionally, non-noble-metal compound.

15. The process as claimed in claim 1, wherein the supported catalyst is employed in a grain size of from 1 to 20 mm.

16. The process as claimed in claim 1, wherein the substituents $R^4$ are themselves substituted by halogen, methoxy, ethoxy or $C_1$ to $C_3$-alkyl groups.

17. The process as claimed in claim 1, wherein substituent Z denotes ortho-, meta- or para-substituted phenylene.

* * * * *

UNITED STATES PATENT AND TRADEMARK OFFICE
CERTIFICATE OF CORRECTION

PATENT NO. : 4,952,727

DATED : AUGUST 28, 1990

INVENTOR(S) : LUFT ET AL.

It is certified that error appears in the above-identified patent and that said Letters Patent is hereby corrected as shown below:

Title Page:
In the designation of the Assignee, item [73] in the left-hand column on the face of the patent, correct the address of Hoechst Aktiengesellschaft to read: --Frankfurt/Main 80, Germany--.

Signed and Sealed this

Ninth Day of June, 1992

Attest:

DOUGLAS B. COMER

*Attesting Officer*  *Acting Commissioner of Patents and Trademarks*

UNITED STATES PATENT AND TRADEMARK OFFICE
CERTIFICATE OF CORRECTION

PATENT NO. : 4,952,727

DATED : August 28, 1990

INVENTOR(S) : Luft, et al

It is certified that error appears in the above-identified patent and that said Letters Patent is hereby corrected as shown below:

On the title page:

Item [22] on the face of the patent, the correct filing date is:
--March 3, 1989--.

Signed and Sealed this

Seventh Day of July, 1992

Attest:

DOUGLAS B. COMER

*Attesting Officer*    Acting Commissioner of Patents and Trademarks